United States Patent [19]
Rosenthal

[11] Patent Number: 5,703,364
[45] Date of Patent: Dec. 30, 1997

[54] METHOD AND APPARATUS FOR NEAR-INFRARED QUANTITATIVE ANALYSIS

[75] Inventor: Robert D. Rosenthal, Gaithersburg, Md.

[73] Assignee: Futrex, Inc., Gaithersburg, Md.

[21] Appl. No.: 601,858

[22] Filed: Feb. 15, 1996

[51] Int. Cl.$^6$ .................................................. G01N 21/35
[52] U.S. Cl. ............................................... 250/339.12
[58] Field of Search ................................... 250/339.12

[56] References Cited

U.S. PATENT DOCUMENTS

| | | | |
|---|---|---|---|
| 4,286,327 | 8/1981 | Rosenthal et al. | 250/339.02 |
| 4,883,963 | 11/1989 | Kemeny et al. | 250/339.07 |
| 5,365,066 | 11/1994 | Krueger, Jr. et al. | 250/341.2 |

Primary Examiner—Constantine Hannaher
Attorney, Agent, or Firm—Rothwell, Figg, Ernst & Kurz

[57] ABSTRACT

Method and apparatus for performing near-infrared (NIR) quantitative analysis includes the steps of providing NIR radiation at a plurality of different wavelengths for illumination of an object to be analyzed, and varying the amount of time that radiation at each wavelength illuminates the subject according to the output level of radiation at each wavelength so as to provide substantially similar detection data resolution for each of the plurality of wavelengths. The method is particularly applicable to non-invasive quantitative measurement of blood analytes such as blood glucose levels, using low cost IREDs operating outside their one-half power bandwidths.

15 Claims, 8 Drawing Sheets

TIME VARIED DEPENDENT ON DETECTOR OUTPUT

|←————————————— ONE CYCLE —————————————→|

| t | 2t | 4t | t | 2t | t | t | t | 1.5t | t | 3t | 4t | 6t | 6t | INCREASE IN TIME |
|---|---|---|---|---|---|---|---|---|---|---|---|---|---|---|
| 1 | 2 | 3 | 4 | 5 | 6 | 7 | 8 | 9 | 10 | 11 | 12 | 13 | 14 | DARK | FILTER # |

(USED IN FIGURE 6A)         = 2.4 x (ORIGINAL SCAN TIME)

EQUAL TIME FOR EVERY FILTER (USED IN FIGURE 4)

TIME VARIED DEPENDENT ON DETECTOR OUTPUT

= 2.4 × (ORIGINAL SCAN TIME)

(USED IN FIGURE 6A)

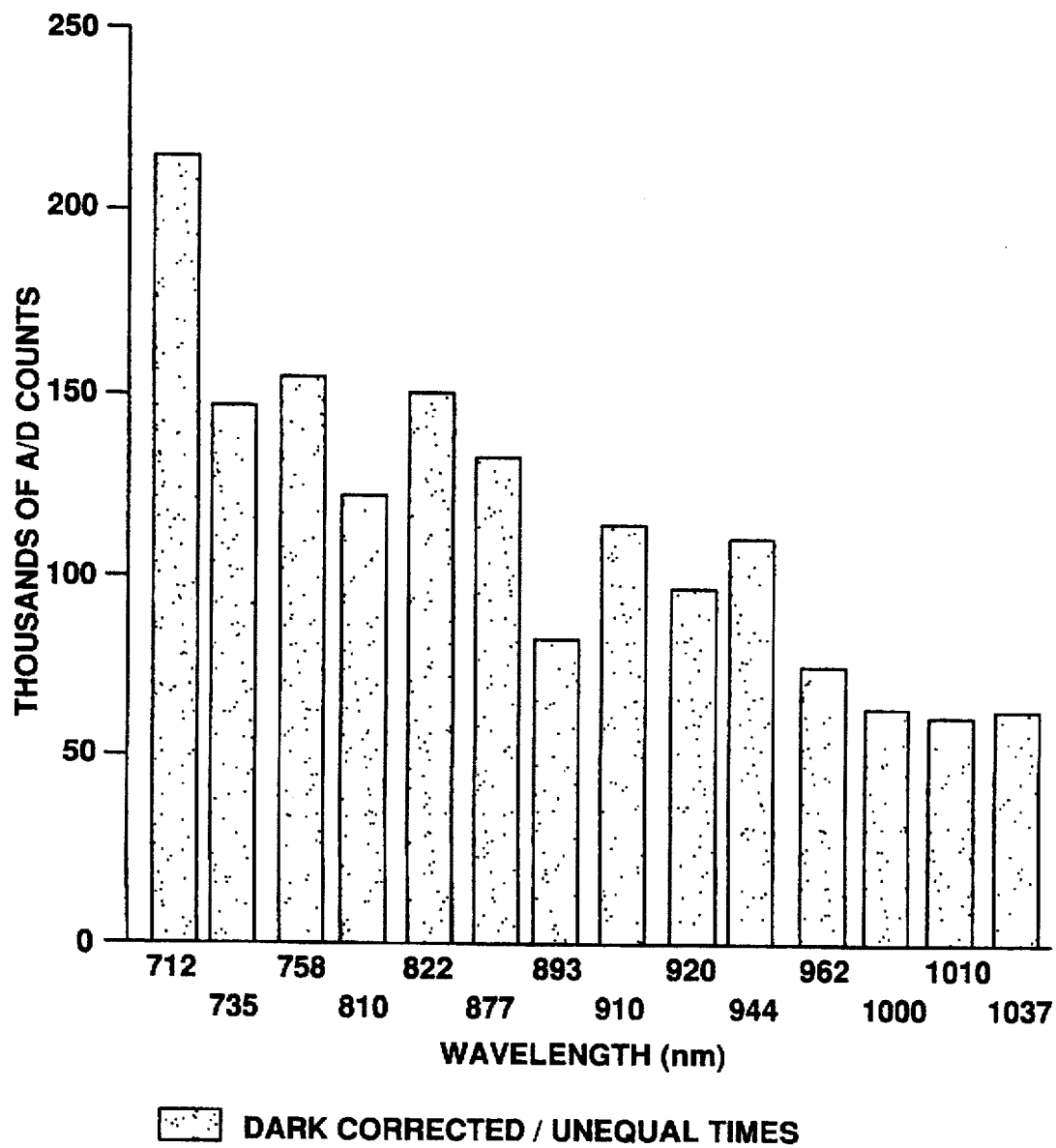

5,703,364

METHOD AND APPARATUS FOR NEAR-INFRARED QUANTITATIVE ANALYSIS

BACKGROUND OF THE INVENTION

1. Field of the Invention

This invention relates to instruments for the non-invasive quantitative measurement of constituents in samples, such as blood glucose levels in the blood, fat content in meats, moisture content in corn, etc. Specifically, this invention relates to improvements in methods and apparatus for near-infrared quantitative analysis.

2. Background and Related Art

The use of quantitative near-infrared (NIR) analysis for the determination of chemical and/or physical characteristics of products is well known in the art. See "An Introduction to Near Infrared Quantitative Analysis," by Robert D. Rosenthal, presented at the 1977 Annual Meeting of the American Association of Cereal Chemists, (1978). See also U.S. Pat. No. 4,286,327 to Rosenthal et al., issued Aug. 25, 1981.

Another known application of NIR analysis relates to the quantitative measurement of analytes in mammals, such as quantitative analysis of glucose in the blood. Information concerning the chemical composition of blood is widely used to assess the health characteristics of both people and animals. Analysis of the glucose content of blood provides an indication of the current status of metabolism. Blood analysis, by the detection of above or below normal levels of various substances, also provides a direct indication of the presence of certain types of diseases and dysfunctions.

In particular, the noninvasive near-infrared quantitative measurement apparatus has particular application for use by diabetics in monitoring the level of glucose in the blood. See U.S. Pat. No. 5,028,787, Rosenthal et al., issued Jul. 2, 1991.

Quantitative NIR analysis is based on the principle that most organic (and some inorganic) substances absorb radiation in the near-infrared range, different substances having different absorption characteristics over specific NIR wavelength ranges. These different characteristics are then used to formulate specific measurement algorithms for obtaining quantitative information regarding the presence of such substances in the subject sample, product, or patient.

To obtain sufficient measurement data for use in such algorithms, it is usually necessary to take a number of measurements, each at a different wavelength. Thus, most NIR quantitative measurement instruments use narrow bandwidth optical filters to provide NIR energy at selected wavelengths.

One prior art method of generating NIR energy at different wavelengths is shown in FIG. 1. A light source (such as a conventional light bulb) 2 is used to illuminate a rotating opaque disk 4. Disk 4 contains a number of narrow bandpass optical filters 6. The disk 4 is rotated by an encoder/stepper motor 8 so that each of the narrow bandpass filters 6 passes under the light beam from the light source 2. The encoder provides a signal indicating the angle of the optical disk with respect to a reference point, and thus provides an indication of which optical filter is presently under the light source.

Light that impinges upon the filters is then filtered such that most of the light is absorbed by the filter, with only a narrow selected wavelength range passing through the filter to illuminate a sample 10. Optical detectors 12 are positioned to detect light which either is reflected by the sample or is transmitted through the sample. The amount of detected light is then measured, which provides an indication of the amount of absorbance of the light by the substance under analysis. Under this approach, the disk is rotated in a manner such that the amount of time that a specific filter is in the path of the light beam from the light source is the same for each filter.

Another system is disclosed by the above-mentioned '327 patent. This patent teaches the use of infrared emitting diodes (IREDs) as sources of near-infrared radiation. As shown in FIG. 2, a plurality (eight in the figure) of IREDs 10 are arranged over a sample WS to be illuminated for quantitative analysis. Near-infrared radiation emitted from each IRED impinges upon an accompanying optical filter 12. Each optical filter is a narrow bandpass filter which passes NIR radiation at a different wavelength. Light baffles 14 are provided between IREDs to prevent light from one IRED being transmitted through an adjacent filter. In the example, the sample WS is held in a holder 16 having a transparent bottom 18. NIR radiation passing through the sample is detected by a detector 20 (such as a silicon photodetector) and converted to an electrical signal which is processed by processing circuitry including an amplifier 22, logarithmic amplifier 23, and analog-to-digital converter 24, and inputted to microprocessor 11. The microprocessor processes the data from the detector using preprogrammed algorithms, to obtain a quantitative measurement of the analyte of interest in the sample, and outputs the result on a display 26. In the system disclosed by the '327 patent, the microprocessor 11 was programmed to sequentially turn on individual IREDs 10, while keeping all other IREDs off, such that each IRED illuminated the sample for an equal amount of time.

The '327 patent further taught the use of low cost sources of NIR radiation, such as gallium arsenide IREDs, which emit near-infrared radiation at a center wavelength of about 940 nm, to obtain radiation at wavelengths up to about 1100 nm, by providing narrow bandpass optical filters having passbands which transmit radiation outside the one-half power bandwidth of the IRED. Thus, different desired wavelengths such as 997, 1007, 1022, 1036.5, and 1057 nm are obtained through the use of appropriate optical filters. Such low cost IREDs are about one-third the cost of indium gallium arsenide IREDs which have center wavelength output between 1000 and 1100 nm.

As shown in FIG. 3, the one-half power bandwidth encompasses the range of wavelengths having output energy of at least one-half of the maximum energy, which is outputted at the center wavelength. A shortcoming in this technique is that radiation at wavelengths outside the one-half power bandwidth of the NIR source is of very low energy, which results in reduced data resolution. Low data resolution of NIR absorption could have a detrimental impact on the accuracy of the measurement in some applications.

FIG. 4 illustrates a prior art instrument for noninvasive measurement of blood analytes, as disclosed in U.S. Pat. No. 5,077,476, issued Dec. 31, 1991, by the same inventor herein. A detailed description of instrument 1 and its operation is provided by the '476 patent, is incorporated by reference herein, and will not be repeated here. In brief summary, the instrument 1 uses a number of low-cost IREDs (50, 60 as shown in FIG. 4) for irradiating a body part, such as the finger, with NIR radiation at selected wavelengths. Narrow bandpass optical filters 160 and 170 are positioned at the output of the IREDs to pass NIR radiation at a selected wavelength. The radiation passes through a window 140, through the subject, and is detected by a detector 80. Light baffle 40 is provided to isolate the various IREDs to prevent radiation from one IRED passing through the optical filter associated with a different IRED.

The detector 80 outputs a signal to microprocessor 100 through amplifier 9. The microprocessor calculates the concentration of analyte at issue (such as blood glucose) and outputs the numerical result to a display device 180. In this instrument, timing and control circuitry 110 is provided which functions to sequentially and individually turn on and off each IRED, one at a time, so that the absorption by the blood analyte and other substances may be measured at each particular wavelength specified in the measurement algorithm. As taught in the '476 patent, the timing and control circuitry 110 operated so as to turn each IRED on for the same amount of time. The range of wavelengths produced by the IREDs is preferably on the order of 600–1100 nm.

FIG. 5 is a graph which shows a typical response of the NIR non-invasive quantitative measurement instrument to NIR radiation of a number of different wavelengths (14 in the example) transmitted through a human finger, when each IRED is turned on for the same amount of time. The horizontal axis represents wavelength in nanometers and the vertical axis represents the number of A/D converter counts received by the instrument as detected by the detector. As seen, radiation at wavelengths far outside the one-half power bandwidth, such as at 1037 nm, the response of the detector is significantly lowered. As previously stated, this reduced response may adversely affect the accuracy of the quantitative measurement result for some applications.

SUMMARY OF THE INVENTION

The present invention provides a near-infrared quantitative analysis instrument and method for near-infrared quantitative analysis which solves the above-mentioned problems.

The present invention further provides a method and apparatus for performing NIR quantitative analysis which utilizes variable turn-on times for different wavelengths of source radiation to increase the total amount of energy detected at wavelengths of weaker output levels. By varying the turn-on times, the data resolution of detected radiation at those otherwise weak wavelengths is significantly increased, which in turn provides increased accuracy of quantitative measurements.

In particular, the present invention provides a method for performing near-infrared (NIR) quantitative analysis, comprising the steps of providing NIR radiation at a plurality of different wavelengths for illumination of an object to be analyzed, detecting NIR radiation transmitted through said subject and accumulating detection data for each of said plurality of wavelengths, and varying the amount of time that radiation at each wavelength illuminates said subject according to the output level of radiation at each wavelength so as to provide substantially similar detection data resolution for each of said plurality of wavelengths.

According to another aspect, the present invention provides apparatus for carrying out the above method.

BRIEF DESCRIPTION OF THE DRAWINGS

The present invention will become more clearly understood from the following detailed description in conjunction with the following drawings, wherein:

FIG. 7 is a graph depicting the response of a non-invasive quantitative measurement instrument as a result of the use of the present invention.

DETAILED DESCRIPTION OF THE PREFERRED EMBODIMENTS

Figure 5:
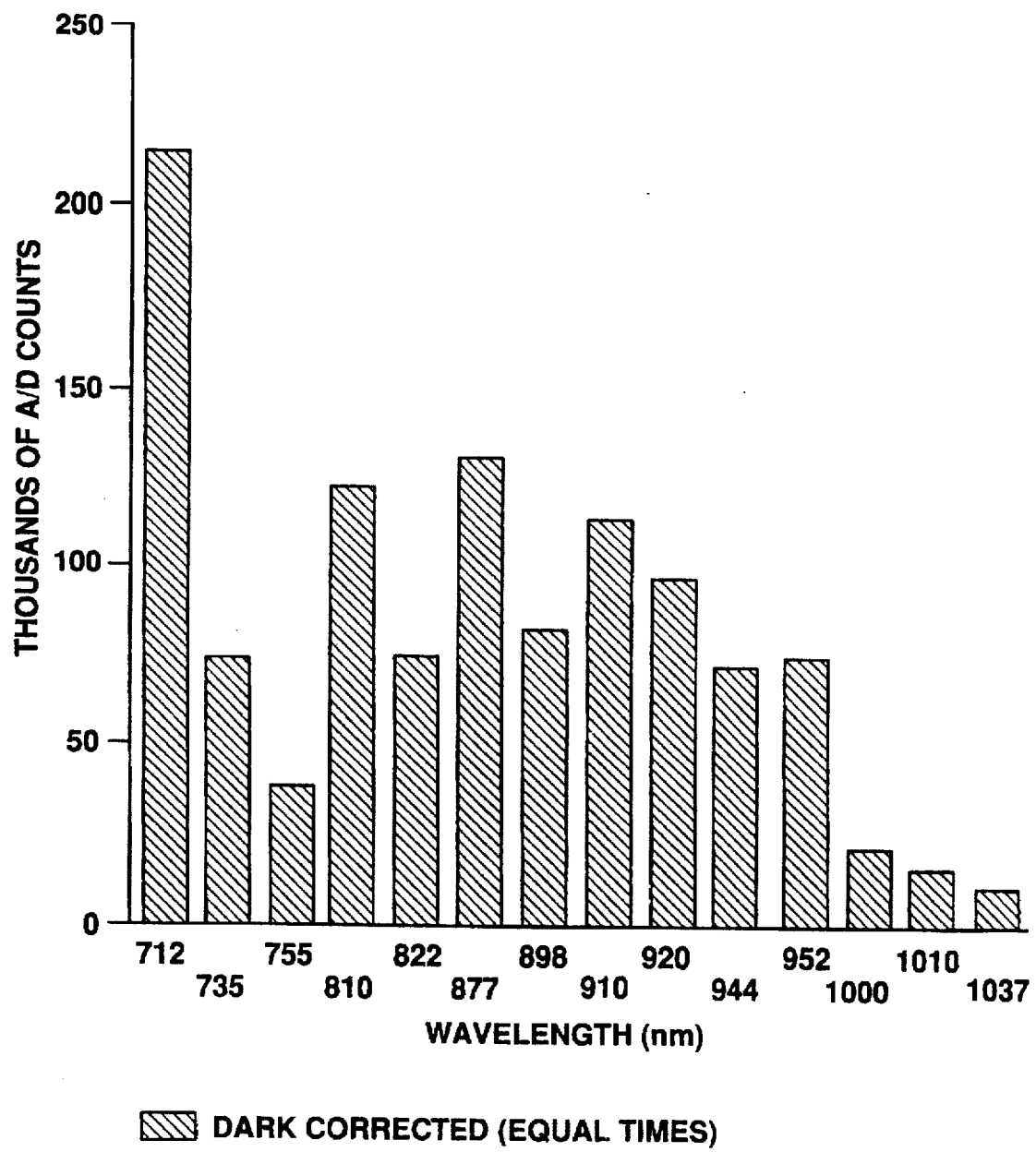
FIG. 5 is a graph depicting the response of the prior art non-invasive measurement instrument to different wavelengths of NIR radiation transmitted through the human hand according to the prior art methodology.
Figure 6A:
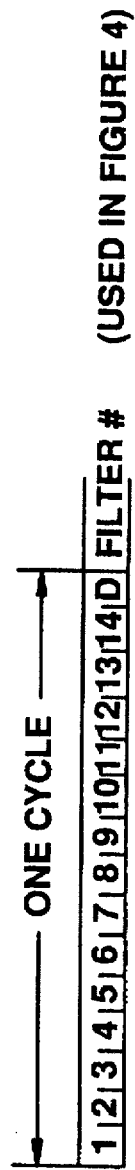
FIGS. 6a and 6b are graphs respectively illustrating the prior art method of energizing IREDs to provide NIR radiation at different wavelengths, and one preferred embodiment of the method of the present invention for performing NIR quantitative analysis.

FIG. 6a illustrates the conventional method for energizing individual IREDs for use in NIR quantitative analysis. FIG. 6a shows the case where 14 IREDs are used with 14 narrow bandpass filters to obtain optical absorption data for NIR radiation at 14 different wavelengths, corresponding to the wavelengths shown in FIG. 5. As shown, according to the prior art, each IRED was sequentially energized for an identical period of time, until all IREDs had been individually energized, at which time the cycle would be repeated. For certain applications, the completion of a cycle would be followed by a "dark period" (D) of equal time period before starting the next cycle of illumination.

Figure 6B:
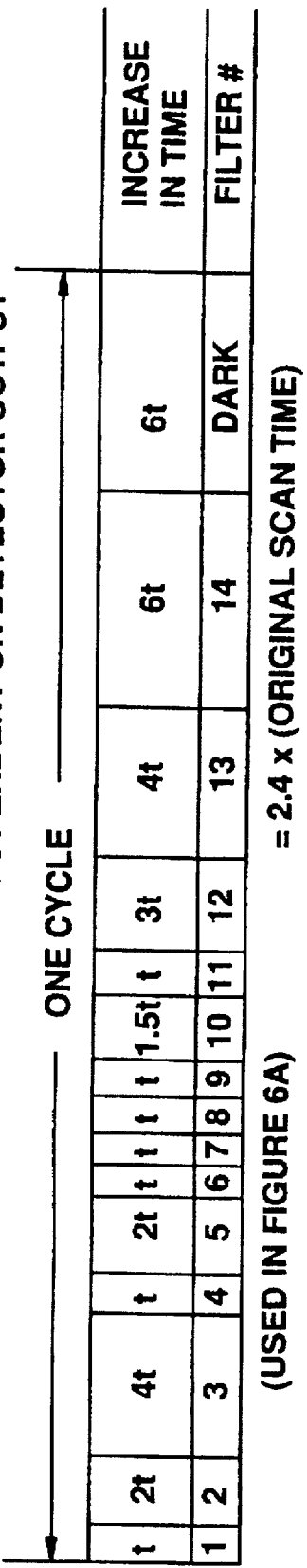

FIG. 6b illustrates one embodiment of the present invention, wherein an instrument having 14 IREDs with associated narrow bandpass filters is used (wherein each IRED and filter outputs a wavelength corresponding to a wavelength in FIG. 7).

As shown, IREDs 1, 4, 6–9 and 11 are each energized for the same amount of time t. IREDs 2 and 5 are energized for a time 2t, IREDs 3 and 13 are energized for a time 4t, IRED 10 is energized for a time 1.5t, IRED 12 is energized for a time 3t, and IRED 14 is energized for a time 6t, followed by a dark period lasting for a time 6t, before the cycle is completed.

Figure 1:
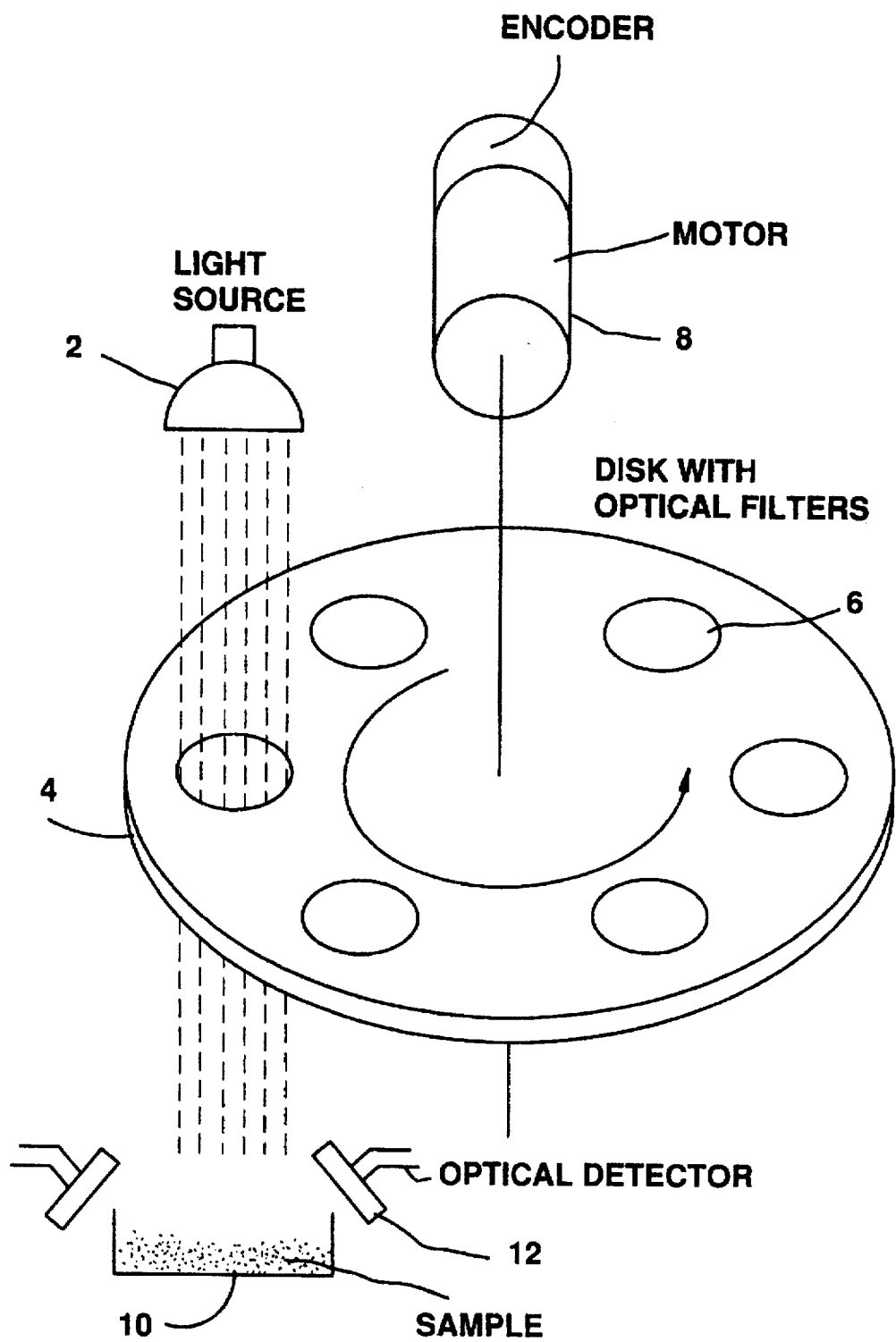
FIG. 1 illustrates one known prior art apparatus for providing different individual wavelengths of electromagnetic radiation useful in NIR quantitative analysis measurements.
Figure 2:
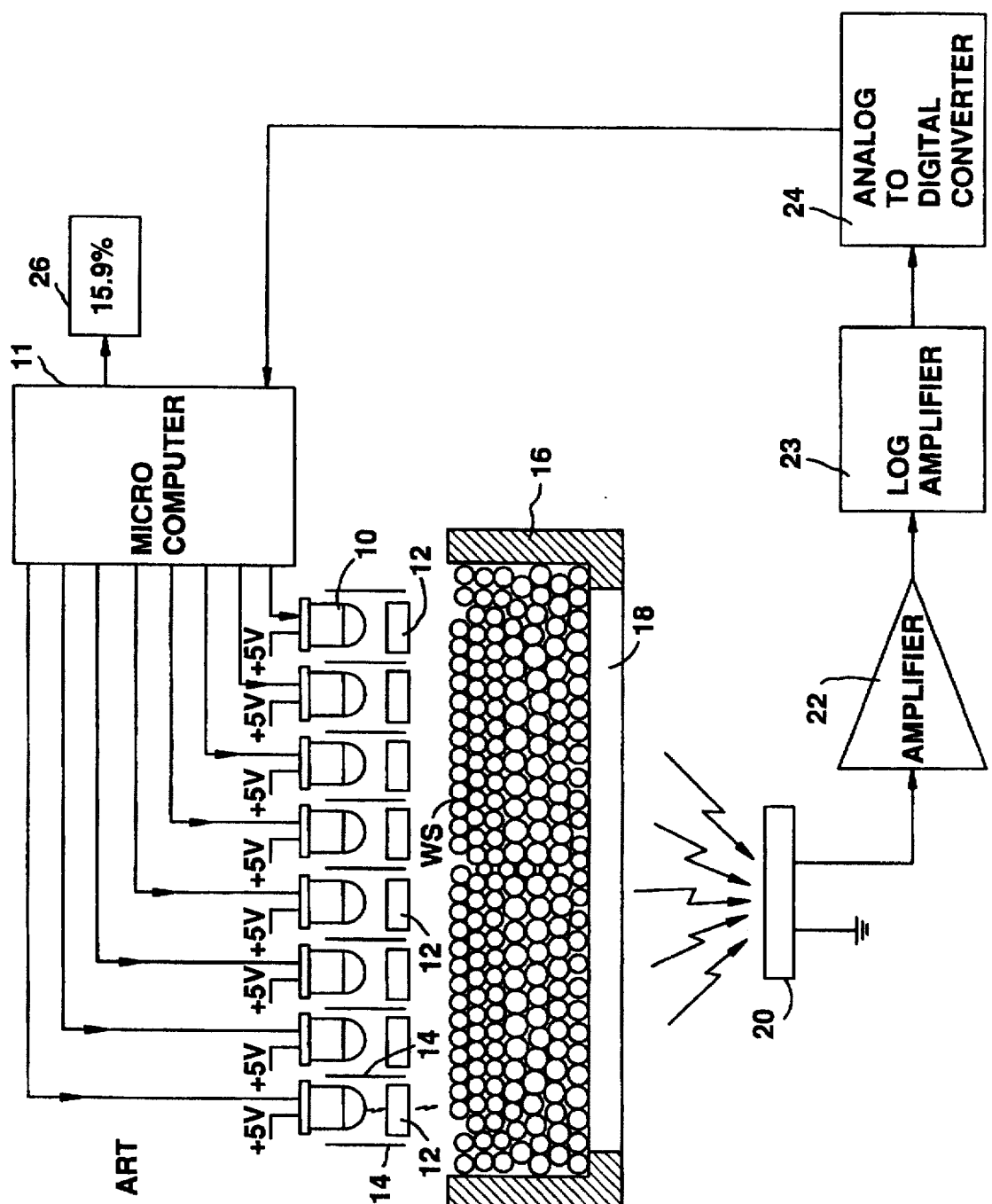
FIG. 2 illustrates an alternative known prior art apparatus for providing different individual wavelengths of electromagnetic radiation useful in NIR quantitative analysis measurements.
Figure 3:
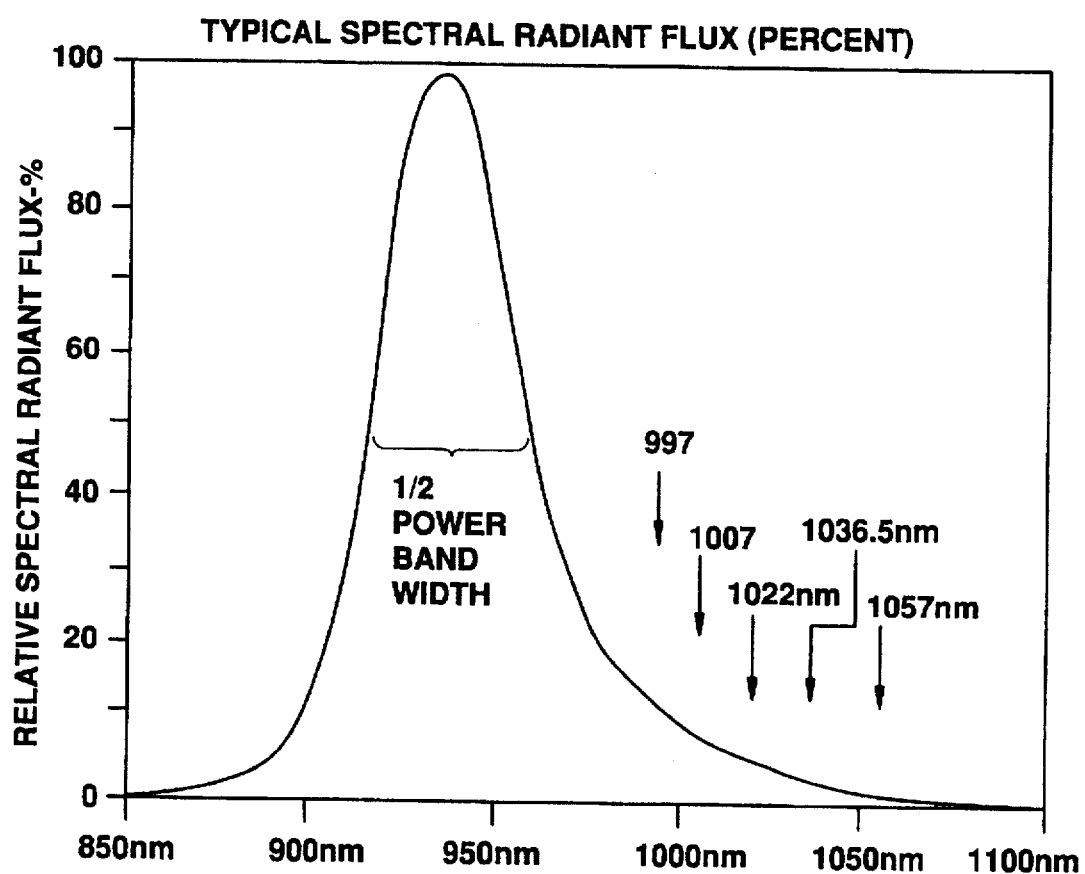
FIG. 3 is a graph showing the radiant flux spectrum of a low cost IRED.
Figure 4:
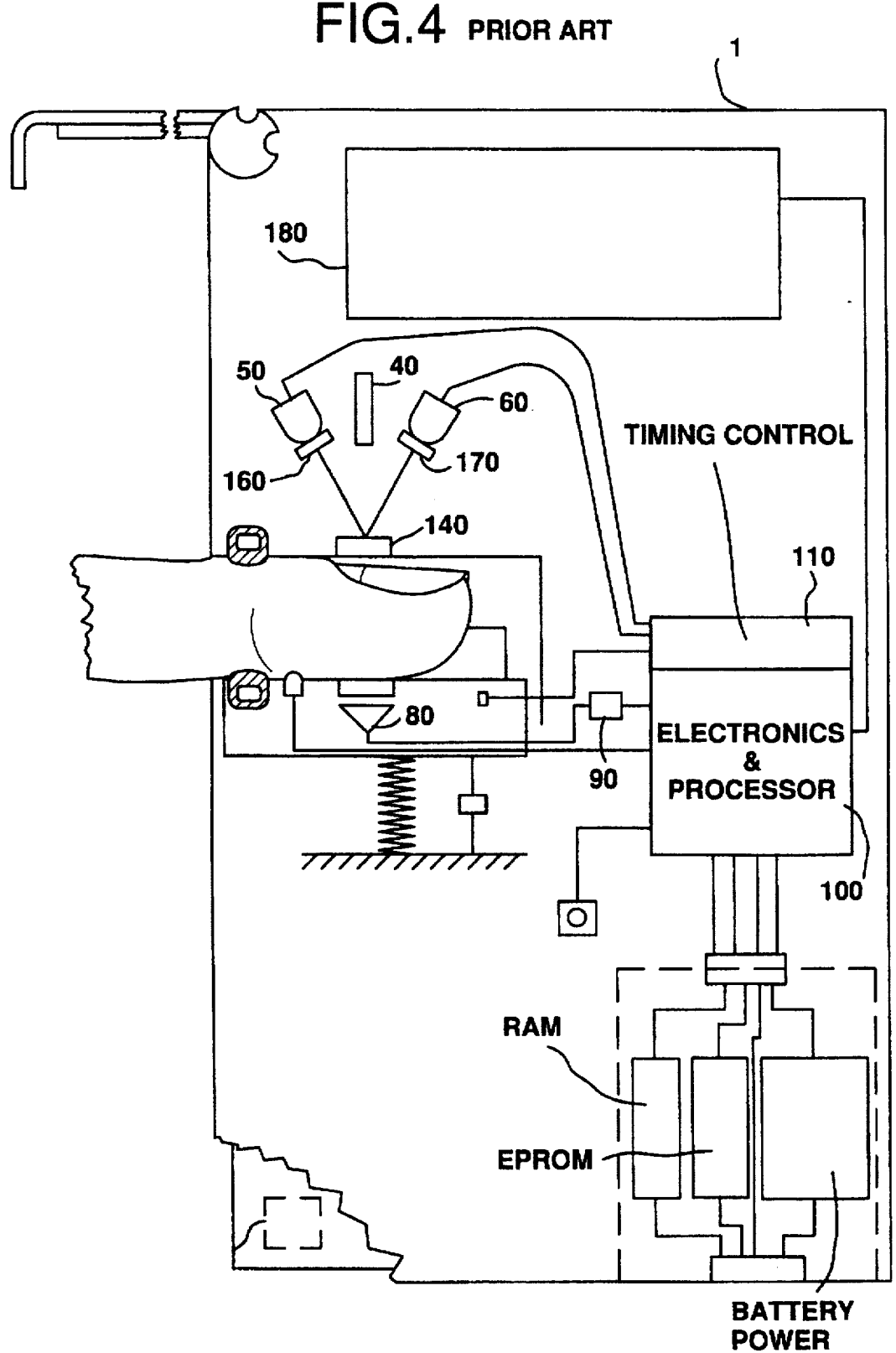
FIG. 4 shows a prior art non-invasive quantitative blood analyte measurement instrument which utilizes low cost IREDs as sources of NIR radiation.

This method of control of the IRED energization is readily carried out by appropriately programming the timing control 110 of the microprocessor 100 shown in FIG. 4. In practice, the specific time periods for each IRED and filter combination can be determined through repeated measurements of a standard sample with different energization times for each instance, in order to optimize the response of the instrument according to the particular measurement and algorithm being used.

FIG. 7 is a graph which shows a typical response of an NIR non-invasive quantitative measurement instrument to NIR radiation of 14 different wavelengths transmitted through a human finger, when each IRED is turned on for the amounts of time shown in FIG. 6b. As seen in comparison with FIG. 5, the previously weak response of the instrument to wavelengths at lower output levels, has been significantly increased so as to provide detection data of substantial similar resolution as that for stronger wavelengths.

The variable time energization approach of the present invention is valid independently of the type of A/D converter used in the instrument. For example, in the case of SAR (successive approximation) type A/D converters, additional conversion bits at the weaker wavelengths would be used for the additional resolution. The resulting data would then be normalized by dividing by the time that the particular IRED is turned on. Similar mathematical adjustments can be applied for integrating type A/D converters.

Figure 8:
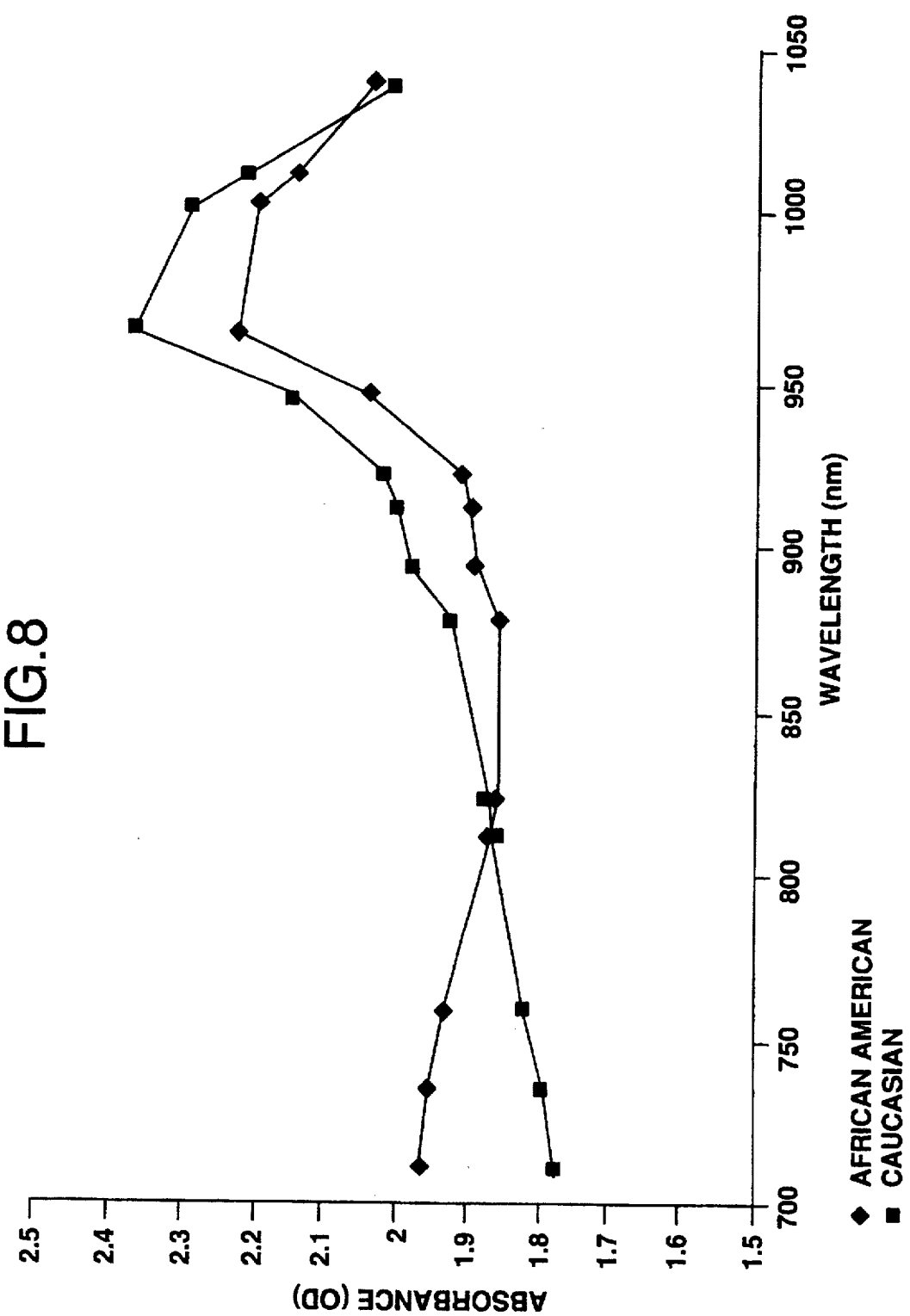
FIG. 8 is a graph illustrating typical optical absorption characteristics of persons of diverse racial origin, which characteristics may be normalized by use of the present invention.

As shown in FIG. 8, people of African ancestry have higher absorption at shorter wavelengths than Caucasians. Conventionally, this higher absorption causes low detector signals at such wavelengths, causing a decrease in resolution. This problem may be solved by the present invention by causing the microprocessor to lengthen the time of energization of those IREDs and filters outputting short wavelength radiation according to the absorption characteristics of the particular individual using the instrument.

In summary, the present invention provides a significant improvement in the accuracy of NIR quantitative measurements by virtue of adjusting the time of energization of each NIR wavelength source according to the level of output at that wavelength.

The invention having been thus described, it will be apparent to those skilled in the art that the same may be varied in many ways without departing from the spirit and scope of the invention. Any and all such modifications are intended to be included within the scope of the following claims.

What is claimed is:

1. A method for performing near-infrared (NIR) quantitative analysis, comprising the steps of:
   providing NIR radiation at a plurality of different wavelengths for illumination of an object to be analyzed;
   detecting NIR radiation transmitted through said object and accumulating detection data for each of said plurality of wavelengths; and
   varying the amount of time that radiation at each wavelength illuminates said object according to the output level of radiation at each wavelength so as to provide substantially similar detection data resolution for each of said plurality of wavelengths.

2. A method as set forth in claim 1, wherein said NIR quantitative analysis relates to quantitative analysis of blood analytes.

3. A method as set forth in claim 2, wherein said NIR quantitative analysis relates to quantitative analysis of glucose levels in blood.

4. A method as set forth in claim 1, wherein said step of providing NIR radiation comprises the step of providing a plurality of IREDs (infrared emitting diodes) and associated narrow bandpass optical filters having passbands at different wavelengths, and sequentially energizing each of said IREDs.

5. A method as set forth in claim 4, wherein each of said plurality of IREDs has a specific NIR energy bandwidth, and at least one of said optical filters transmits NIR radiation outside the one-half power bandwidth of its associated IRED.

6. An apparatus for performing near-infrared (NIR) quantitative analysis, comprising:
   means for providing NIR radiation at a plurality of different wavelengths for illumination of an object to be analyzed;
   means for detecting NIR radiation transmitted through said object and accumulating detection data for each of said plurality of wavelengths; and
   means for varying the amount of time that radiation at each wavelength illuminates said object according to the output level of radiation at each wavelength so as to provide substantially similar detection data resolution for each of said plurality of wavelengths.

7. An apparatus as set forth in claim 6, wherein said apparatus performs quantitative analysis of blood analytes.

8. An apparatus as set forth in claim 7, wherein said apparatus performs quantitative analysis of glucose levels in blood.

9. An apparatus as set forth in claim 6, wherein said means for providing NIR radiation comprises a plurality of IREDs (infrared emitting diodes) and associated narrow bandpass optical filters having passbands at different wavelengths, and means for sequentially energizing each of said IREDs.

10. An apparatus as set forth in claim 9, wherein each of said plurality of IREDs have specific NIR energy bandwidths, and at least one of said optical filters has a passband outside the one-half power bandwidth of its associated IRED.

11. A near-infrared quantitative analysis instrument for non-invasive measurement of analytes in blood present in a body part of a subject, comprising:
   means for providing near-infrared energy at a plurality of different wavelengths for introduction into blood present in a body part of a subject;
   detecting means for detecting near-infrared energy emerging from said body part of said subject and providing a signal representative of the amount of near-infrared energy being detected;
   processing means for receiving signals from said detecting means and for processing said signals to determine the quantity of a specific analyte in said blood; and
   means for energizing said providing means in such manner to sequentially provide at least two different wavelengths of near-infrared energy each for a different amount of time.

12. A near-infrared quantitative analysis instrument as set forth in claim 11, wherein said at least two different wavelengths are in the range of about 600 to about 1100 nm.

13. A near-infrared quantitative analysis instrument as set forth in claim 11, wherein said providing means comprises a plurality of IREDs and associated narrow bandpass optical filters, each transmitting near-infrared energy at a different wavelength.

14. A near-infrared quantitative analysis instrument as set forth in claim 13, wherein said IREDs have specific near-infrared energy bandwidths, and at least one of said optical filters passes near-infrared energy outside the one-half power bandwidth of its associated IRED.

15. A near-infrared quantitative analysis instrument as set forth in claim 11, wherein said energizing means comprises a microprocessor programmed to turn on individual IREDs for varying periods of time.

* * * * *